US011371010B2

(12) United States Patent
Martin et al.

(10) Patent No.: US 11,371,010 B2
(45) Date of Patent: *Jun. 28, 2022

(54) PROCESS FOR THE PREPARATION OF ACTIVE PRINCIPLES ON THERMAL WATER AND COMPOSITIONS COMPRISING THEM

(71) Applicant: L'ORÉAL, Paris (FR)

(72) Inventors: Richard Martin, Rochecorbon (FR); Pascal Hilaire, Vouvray (FR)

(73) Assignee: L'ORÉAL, Paris (FR)

( * ) Notice: Subject to any disclaimer, the term of this patent is extended or adjusted under 35 U.S.C. 154(b) by 139 days.

This patent is subject to a terminal disclaimer.

(21) Appl. No.: 15/353,173

(22) Filed: Nov. 16, 2016

(65) Prior Publication Data

US 2017/0226470 A1 Aug. 10, 2017

Related U.S. Application Data

(63) Continuation of application No. 12/599,308, filed as application No. PCT/EP2008/055644 on May 7, 2008, now abandoned.

(60) Provisional application No. 60/945,969, filed on Jun. 25, 2007.

(30) Foreign Application Priority Data

May 10, 2007 (FR) ...................... 0754957

(51) Int. Cl.
| | | |
|---|---|---|
| C12N 1/20 | (2006.01) |
| A61K 8/99 | (2017.01) |
| A61K 35/74 | (2015.01) |
| A61Q 19/00 | (2006.01) |
| C12N 1/38 | (2006.01) |
| A61K 8/96 | (2006.01) |
| A61K 35/08 | (2015.01) |
| C12P 19/02 | (2006.01) |
| C12R 1/01 | (2006.01) |

(52) U.S. Cl.
CPC ............... *C12N 1/20* (2013.01); *A61K 8/965* (2013.01); *A61K 8/99* (2013.01); *A61K 35/08* (2013.01); *A61K 35/74* (2013.01); *A61Q 19/00* (2013.01); *C12N 1/205* (2021.05); *C12N 1/38* (2013.01); *C12P 19/02* (2013.01); *C12R 2001/01* (2021.05)

(58) Field of Classification Search
None
See application file for complete search history.

(56) References Cited

U.S. PATENT DOCUMENTS

| | | | |
|---|---|---|---|
| 5,597,558 A | 1/1997 | Aubert et al. | |
| 5,618,521 A | 4/1997 | De Rigal et al. | |
| 5,690,946 A | 11/1997 | Koulbanis et al. | |
| 5,795,574 A | 8/1998 | Breton et al. | |
| 6,242,229 B1 | 6/2001 | Pineau et al. | |
| 9,125,934 B2 | 9/2015 | Breton et al. | |
| 9,393,266 B2* | 7/2016 | Breton ............... | A61K 8/99 |
| 9,770,474 B2* | 9/2017 | Gueniche ............ | A61K 8/99 |
| 2003/0224077 A1 | 12/2003 | Mahe et al. | |
| 2004/0137023 A1 | 7/2004 | Dalko et al. | |
| 2005/0008666 A1 | 1/2005 | Lalaudiere et al. | |
| 2005/0118118 A1 | 6/2005 | Martin | |

FOREIGN PATENT DOCUMENTS

| | | |
|---|---|---|
| EP | 0 761 204 | 3/1997 |
| EP | 1 166 764 | 1/2002 |
| EP | 1 354 593 | 10/2003 |
| EP | 1 479 367 | 11/2004 |
| FR | 2 283 223 | 3/1976 |
| FR | 2 440 403 | 5/1980 |
| GB | 2 034 687 A | 6/1980 |
| GB | 2 189 505 A | 10/1987 |
| JP | 56-109589 A | 8/1981 |
| JP | 62-48396 A | 3/1987 |
| JP | 62-273911 | 11/1987 |
| JP | 2-503985 A | 11/1990 |
| JP | 8-3015 A | 1/1996 |
| JP | 8-59426 A | 3/1996 |
| JP | 10-511110 A | 10/1998 |
| JP | 10-298085 A | 11/1998 |
| JP | 2000-212062 A | 8/2000 |
| JP | 2004-277406 A | 10/2004 |
| JP | 2004-346073 A | 12/2004 |
| JP | 2005-139188 A | 6/2005 |
| WO | WO 89/04599 | 6/1989 |
| WO | 94 02158 | 2/1994 |
| WO | WO 94/02158 | 2/1994 |
| WO | 2006 095098 | 9/2006 |

OTHER PUBLICATIONS

English translation of Aubert (WO 94/02158)—1994.*
Office Action dated Jul. 2, 2013 in Japanese Application No. 2010-506932 (submitting English translation only).
Collober, I. et al., "Activity of Vittel water on proliferation of human fibroblasts, proliferation and differentiation of human keratinocytes", International Journal of Cosmetic Science, vol. 16. No. 4, pp. 149-160, XP-000953265, (1994).
"Plongez dans l'offre regionale", URL:http://www.ra-sante.com/forme-et-bien-etre/bien-etre/spa-et-thermalisme/plongez-dans-l-offre-regionale-20070601.htm, 3 pages, XP-002452939, (Jun. 1, 2007).
"Thermes des Fumades-les-bains", URL:http://www.cosmetherm.fr/thermes.htm, 2 pages, XP-002452940, (Mar. 19, 2003).
"Les Eaux Bonnes", URL:http://web.archive.org/web/20070208003605/http://www.pyrenees-decouvertes.com/sommaire/sport/therm/eaux/index.php, 1 page, XP-002452941, (Feb. 8, 2007).

(Continued)

*Primary Examiner* — Susan Hoffman
(74) *Attorney, Agent, or Firm* — Oblon, McClelland, Maier & Neustadt, L.L.P.

(57) ABSTRACT

The invention relates to a process for the preparation of a cosmetic or dermatological active principle, comprising the culturing of at least one nonphotosynthetic and nonfruiting filamentous bacterium on a medium comprising at least one nonsulphurous mineral and/or thermal water.
It also relates to a cosmetic or dermatological composition comprising at least one bacterium of the genus *Vitreoscilla* or one of its extracts.

17 Claims, No Drawings

(56) References Cited

OTHER PUBLICATIONS

"Urie eau thermale", URL http://web.archive.org/web/20051220080625/http://www.laroche-posay.org/guide+2005/eau.pdf, 1 page, XP-002452942, (Dec. 20, 2005).
"Vittel", URL:http://web.arhive.org/web/20060116023024/http://www.vittel.be/fr/composition.aspx, 1 page, XP-002452943, (Jan. 16, 2006).
Gueniche, A., et al. 2006 ESDR Abstracts, p. S99 (Jul.-Aug. 2006). *Vitreoscilla filiformis* bacterium extract improves seborrheic dermatitis.

* cited by examiner

PROCESS FOR THE PREPARATION OF ACTIVE PRINCIPLES ON THERMAL WATER AND COMPOSITIONS COMPRISING THEM

The present invention relates to novel processes for culturing microorganisms, of use in particular in the cosmetics or pharmaceutical field, which confer improved properties thereon. It also relates to the use of bacteria capable of being obtained by these processes, or their extracts, in the preparation of compositions in particular having a cosmetic or dermatological use.

The invention relates in particular to the culturing of nonphotosynthetic and nonfruiting filamentous bacteria as defined according to the classification of Bergey's Manual of Systematic Bacteriology (vol. 3, sections 22 and 23, 9th edition, 1989), among which may be mentioned the bacteria belonging to the order of the Beggiatoales and more particularly the bacteria belonging to the genera *Beggiatoa, Vitreoscilla, Flexithrix* or *Leucothrix*.

The culturing of such bacteria of the family of the Beggiatoaceae has been described in Application FR 2 283 223, by multiplication in a fermenter in a weakly stirred medium.

Application WO 94/02158 teaches the preparation of immunomodulating compositions from envelopes of bacteria of the genus *Beggiatoa* or *Vitreoscilla*. The bacteria are cultured on a medium prepared with distilled water and a monosaccharide, in particular glucose, as carbon source.

Furthermore, the filamentous bacteria thus obtained, or fractions, exhibit advantageous properties which have been described, for example, for combating signs of ageing in EP 681 831 or for treating sensitive skin in EP 761 204.

There still exists a need to find improved processes for producing such microorganisms.

It has been found, in the context of the present invention, that the replacement, in all or part, of the distilled water conventionally present in the medium for culturing filamentous bacteria by mineral water makes it possible to obtain a bacterial mass exhibiting improved properties.

This is why a subject-matter of the present invention is a process for the preparation of a cosmetic or dermatological active principle, comprising the culturing of at least one nonphotosynthetic and non-fruiting filamentous bacterium on a medium comprising at least one mineral and/or thermal water which is preferably nonsulphurous.

As indicated above, the nonphotosynthetic filamentous bacteria comprise in particular the bacteria belonging to the order of the Beggiatoales and more particularly the bacteria belonging to the genera *Beggiatoa, Vitreoscilla, Flexithrix* or *Leucothrix*.

The process according to the invention is particularly suitable for the culturing of bacteria belonging to the genus *Vitreoscilla*, in particular for bacteria of the species *Vitreoscilla filiformis*.

The bacteria which have just been defined, several of which have already been described, generally have an aquatic habitat and can be found in particular in sea waters or in thermal waters. Mention may be made, among the bacteria which can be used, for example, of:
*Vitreoscilla filiformis* (ATCC 15551)
*Vitreoscilla beggiatoides* (ATCC 43181)
*Beggiatoa alba* (ATCC 33555)
*Flexithrix dorotheae* (ATCC 23163)
*Leucothrix mucor* (ATCC 25107)
*Sphaerotilus natans* (ATCC 13338)

Preferably, the process according to the invention is applied to the culturing of the bacterium corresponding to the strain deposited at the ATCC under No. 15551.

The term "thermal water" is understood to mean a hot or cold water which is used for its therapeutic powers or for a bathing use. The present invention can use a thermal water or a mineral water. Generally, a mineral water is suitable for consumption, which is not always the case with a thermal water. Each of these waters comprises, inter alia, dissolved minerals and trace elements. These waters are known to be employed for specific treatment purposes depending on the particular trace elements and minerals present therein.

Preferably, in the process according to the invention, use is made of a thermal and/or mineral water which exhibits a total mineral content of greater than or equal to 400 mg/l.

In the invention, the term "total mineral content" is understood to mean the sum of the concentrations of anions and cations present in the thermal or mineral water. In the thermal or mineral waters of use according to the invention, the total mineral content is generally between 400 and 900 mg/l.

The thermal and/or mineral water used according to the invention can have a total mineral content of at least 700 mg/l, in particular a total concentration of carbonates and of bicarbonates of at least 150 mg/l and more preferably of at least 360 mg/l and in particular of sodium carbonate and bicarbonate of greater than 2 mg/l. The concentration of silicon oxide in the water used in the composition according to the invention can preferably be at least 6 mg/l and more preferably at least 9 mg/l.

The thermal water or the mineral water used according to the invention can be chosen from water from Vittel, waters from the Vichy basin, water from Uriage, water from La Roche-Posay, water from La Bourboule, water from Enghien-les-Bains, water from Saint Gervais-les-Bains, water from Néris-les-Bains, water from Allevard-les-Bains, water from Digne, water from Maizières, water from Neyrac-les-Bains, water from Lons-le-Saunier, water from Eaux-Bonnes, water from Rochefort, water from Saint Christau, water from Les Fumades and water from Tercis-les-Bains.

Among these waters, those which exhibit a total concentration of carbonates or bicarbonates of greater than 360 mg/l are water from Vittel, water from La Bourboule, water from Les Fumades, water from Enghien-les-Bains, water from La Roche-Posay, water from the Vichy basin and water from Uriage.

Among these waters, those which exhibit a concentration of carbonates or bicarbonates of between 150 mg/l and 360 mg/l are water from Digne, water from Maizières, water from Rochefort or water from Saint Gervais-les-Bains.

Among these waters, those which comprise at least 2 mg/l of sodium carbonate or bicarbonate are water from La Roche-Posay, water from Vittel, waters from the Vichy basin or water from Uriage.

The waters comprising at least 9 mg/l of silicon oxide are water from La Roche-Posay, water from Vittel, waters from the Vichy basin or water from Uriage.

The thermal or mineral waters which are particularly suitable for the implementation of the invention have a concentration of calcium ions of greater than or equal to 100 mg/l, indeed even 140 mg/l.

According to an advantageous embodiment, the thermal or mineral water has a concentration of hydrogencarbonate ions of greater than or equal to 300 mg/l. The hydrogencarbonates, also known as bicarbonates, are present in particular at a concentration of greater than or equal to 350 mg/l.

According to an advantageous embodiment, the bacteria are cultured on a medium comprising at least one thermal water. The latter can in particular be chosen from water from Vittel, waters from the Vichy basin, water from Uriage, water from La Roche-Posay, water from La Bourboule, water from Les Fumades, water from Enghien-les-Bains or water from Eaux-Bonnes.

The waters which make it possible to obtain a particular advantageous result according to the invention are chosen in particular from water from La Roche-Posay and water from Vittel, or a water with a similar composition.

Water from La Roche-Posay is extracted from the spring of the same name; it is a water comprising bicarbonate, calcium, silicate and selenium. It generally comprises approximately 387 mg/l of bicarbonate ions, approximately 140 mg/l of calcium ions and at least 40 mg/l of sulphates.

Water from Vittel is rich in calcium and in mineral salts (841 mg/l) and comprises in particular 202 mg/l of calcium, 402 mg/l of bicarbonates and 336 mg/l of sulphates.

Culturing can in particular be carried out in the following medium:

| Composition | Concentration |
|---|---|
| Autolytic yeast extract | 0.5 to 5 g/l |
| Peptone | 05 to 5 g/l |
| Anhydrous glucose | 0.5 to 7 g/l |
| Heller microelements | 0.5 to 5 ml/l |
| $CaCl_2 \cdot 10H_2O$ | 0.010 to 0.200 g/l |

The composition is made up to 1000 ml with distilled water and/or mineral or thermal water.

Mention may be made, among peptones which can be used, for example, of soybean papain peptone.

This medium is distinguished from the media generally used by the absence of catalase and sulphide. The Heller microelements have been described by Heller, Ann. Sci. Nat. Biol. Veg., 14, 1-223 (1953). They are mixtures of various mineral elements which are recommended by Heller not for the culturing of bacteria but for the nutrition of plant tissues cultured in vitro.

Culturing can be carried out at the appropriate temperature suitable for the bacterial species cultured. Generally, this temperature is between 18 and 40° C., depending on the strains. The pH of the culture medium is preferably between 5.5 and 8.

The composition of the Heller microelements, per 1 l of water, is as follows:

$ZnSO_4 \cdot 7H_2O$ . . . 1 g
$MnSO_4 \cdot H_2O$ . . . 0.076 g
$CuSO_4 \cdot 5H_2O$ . . . 0.003 g
KI . . . 0.010 g
$H_3BO_3$ . . . 1 g
$AlCl_3 \cdot 6H_2O$ . . . 0.050 g
$NiCl_2 \cdot 6H_2O$ . . . 0.030 g The said thermal or mineral waters can replace all or part of the aqueous phase of the culture medium. They can thus be found as a mixture in any proportion with the water, in particular distilled or osmotically treated water, present in the culture medium.

After mixing all the elements of the medium, the culture medium comprising the thermal and/or mineral water is advantageously sterilized; this stage is carried out by methods known to a person skilled in the art, such as sterilization by filtration or by heat.

The culture medium is subsequently inoculated with the bacteria.

Another subject-matter of the invention is thus a process for culturing microorganisms or for preparing a cosmetic or dermatological active principle as defined above, characterized in that the culture medium comprises a mixture (i) of osmotically treated or distilled water and (ii) of thermal water, in a ratio (i)/(ii) of between 1 and 100, in particular from 1 to 50, especially from 1 to 25.

Unexpectedly, it has been found, in the context of the invention, that the incorporation of thermal and/or mineral water in the culture medium in a relatively small proportion can confer, on the microorganism, advantageous properties distinct from those of a microorganism cultured on a medium in which the water incorporated is exclusively distilled and/or osmotically treated water.

Thus, in media suitable for the implementation of the invention, the thermal or mineral water preferably represents at least 0.1% of the amount of water introduced for the preparation of the medium, in particular from 0.1 to 99.9%. Good results are obtained with concentrations of thermal water of approximately 1% or 2%, with respect to the osmotically treated and/or distilled water, for example from 0.5 to 20%, indeed even from 0.5 to 50%, but these concentrations can be increased without disadvantage.

In a known way, the process comprises at least one stage in which the bacteria are recovered at the end of culturing, in particular by separating them from the culture medium.

After culturing the bacteria, the biomass can be isolated by various known methods, for example by filtration, by coagulation with an alcohol (ethanol, isopropanol, isobutanol), by drying on a cylinder with a scraped prelayer (starch, diatoms, and the like) or by lyophilization. A preliminary concentration, for example at 80° C. under reduced pressure, improves this separation.

An operation of rupturing the envelopes can be carried out, for example by the action of ultrasound. In addition, extracts can be prepared using an alcohol, such as ethanol or propanol.

Lipopolysaccharide extracts can also be prepared according to known methods; for example, see Noris and Ribbons, Methods in Microbiology, Vol. 5B, Academic Press (1971). The method generally used is the well-known "Westphal" method (or a related method), which consists in carrying out the extraction with phenol/water mixtures at 65° C. The extract is subsequently subjected to dialysis in order to remove the phenol.

The invention relates in particular to a process for the preparation of a cosmetic or dermatological active principle as defined above, characterized in that it comprises a stage during which (i) at least one bacterium belonging to the order of the Beggiatoales is cultured on a medium comprising a monosaccharide as main carbon source and at least one mineral or thermal water and then (ii), after fermentation, the bacteria are separated from the culture medium in order to recover the said mass of the bacteria.

The bacteria recovered on conclusion of the fermentation stage can in particular be subjected to a stabilization and/or extraction treatment. It is the extract of filamentous bacteria which is thus obtained which will generally be used in or for the preparation of cosmetic or dermatological compositions. In a way known per se, the extract can thus be sterilized, in particular by filtration or by autoclaving.

The term "extract of nonphotosynthetic filamentous bacteria" is understood to mean equally well the supernatant from the culturing of the said bacteria, the biomass obtained after culturing the said bacteria or the extracts of the biomass which are obtained by treatment of this biomass.

In order to prepare the extract according to the invention, the said bacteria can be cultured according to the process according to the invention and can then be separated from the biomass obtained, for example by filtration, centrifuging, coagulation and/or lyophilization.

Thus, after culturing, the bacteria are concentrated by centrifuging. The biomass obtained is autoclaved. This biomass can be lyophilized in order to constitute what is referred to as the lyophilized extract. Any lyophilization method known to a person skilled in the art can be used to prepare this extract.

The supernatant fraction from this biomass can also be filtered into a sterile container in order to remove the suspended particles. This supernatant fraction can also be decanted under sterile conditions into a sterile container. According to a specific embodiment of the invention, the supernatant fraction thus obtained is used as cosmetic or dermatological active principle.

Unexpectedly, it has been found, in the context of the present invention, that the culturing of a bacterium on a medium comprising at least one thermal or mineral water, in particular constituting from 1 to 100% of the water present in the culture medium, conferred, on the bacterium obtained on conclusion of the various fermentation and isolation stages, specific properties distinct from those of the same bacterium cultured on a medium not supplemented with thermal and/or mineral water but comprising only osmotically treated or distilled water.

According to another aspect of the invention, the substitution of all or part of the water of the medium for culturing the bacterium by mineral or thermal water makes it possible to increase the rate of growth of the bacterium and thus to improve the production output.

This is why another subject-matter of the invention is the use of at least one thermal or mineral water, which is nonsulphurous, as defined above, as agent for improving the activity and/or the growth of a bacterium of the genus *Vitreoscilla*, in particular *Vitreoscilla filiformis*.

The invention also relates to a process for improving the growth and/or the properties of a bacterium of the genus *Beggiatoa* or *Vitreoscilla* which consists in adding a thermal and/or mineral water to the culture medium in at least one stage of the culturing.

Another subject-matter of the invention is a culture medium suited to the culturing of nonphotosynthetic filamentous bacteria as defined above, the water present in the said medium comprising at least 1% of mineral and/or thermal water, in particular from 1 to 99.9%, preferably from 1 to 25%.

Another subject-matter of the invention is the bacteria, in particular *Vitreoscilla filiformis*, capable of being obtained by the process according to the invention, and also their extracts and their uses in compositions, the bacteria, their extracts or the compositions being of use in improving the condition of the skin and/or superficial body growths.

Another subject-matter of the invention is thus a composition, in particular a cosmetic or dermatological composition, characterized in that it comprises, in a physiologically acceptable medium, at least one bacterium of the genus *Vitreoscilla* capable of being obtained by the process described above, or an extract of the latter.

The compositions used according to the invention can be provided in all the forms suitable for the applications envisaged, in particular orally or topically, in the cosmetic and dermatological fields.

The term "topically" is preferably understood to mean use by topical application to the skin or superficial body growths; the term "skin" also encompasses, unless otherwise indicated, the scalp or mucous membranes.

The composition according to the invention can thus be applied to any cutaneous region of the body, the hair, the nails or the mucous membranes and can be provided in any suitable formulation form by a person skilled in the art. It can in particular be provided in the form of an aqueous or oily solution or suspension, of an oil-in-water or water-in-oil or multiple emulsion, of a silicone emulsion, of a microemulsion or nanoemulsion, of an aqueous or oily gel or of a liquid, pasty or solid anhydrous product.

For topical application to the skin, the composition can have the form in particular of aqueous or oily solutions or of dispersions of the lotion or serum type, of emulsions with a liquid or semiliquid consistency of the milk type, obtained by dispersion of a fatty phase in an aqueous phase (O/W) or vice versa (W/O), or of suspensions or emulsions with a soft consistency of the aqueous or anhydrous cream or gel type, or else of microcapsules or microparticles, or of vesicular dispersions of ionic and/or nonionic type. It can also be presented in the form of a patch or of a controlled release system. These compositions are prepared according to the usual methods.

They can also be used for the hair in the form of aqueous, alcoholic or aqueous/alcoholic solutions, or in the form of creams, gels, emulsions or foams, or also in the form of aerosol compositions also comprising a pressurized propellant.

For the eyes, the composition can be provided in the form of drops and, for ingestion, it can be provided in the form of capsules, granules, gels, chewing pastes, syrups or tablets.

The amounts of the various constituents of the compositions according to the invention are those conventionally used in the fields under consideration.

These compositions constitute in particular creams for cleaning, protecting, treating or caring for the face, for the hands, for the feet, for the major anatomical folds or for the body (for example, day creams, night creams, make-up-removing creams, foundation creams or sun creams), masks to be left standing on the skin or hair, liquid foundations, make-up-removing milks, protective or care body milks, sun milks, lotions, gels or foams for caring for the skin, such as cleansing lotions, sun lotions, artificial tanning lotions, bath compositions, deodorizing compositions comprising a bactericidal agent, aftershave gels or lotions, depilatory creams, compositions for countering insect stings or bites, pain-relieving compositions or compositions for treating certain skin diseases, such as eczema, rosacea, psoriasis, lichen or severe pruritus.

The compositions according to the invention can also consist of solid preparations constituting cleansing soaps or bars.

The compositions can also be packaged in the form of an aerosol composition also comprising a pressurized propellant.

The composition according to the invention can also be a hair-care composition, and in particular a shampoo, a hair-setting lotion, a treating lotion, a styling cream or gel, a dyeing composition (in particular an oxidation dyeing composition), optionally in the form of shampoo dyes, hair restructuring lotions, a perming composition (in particular a composition for the first step of a perming), a lotion or a gel for combating hair loss, an antiparasitic shampoo, and the like.

The composition can also be for oral use, for example, a toothpaste. In this case, the composition can comprise adjuvants and additives conventional for compositions for oral use and in particular surface-active agents, thickening agents, humectants, polishing agents, such as silica, various active ingredients, such as fluorides, in particular sodium fluoride, and optionally sweetening agents, such as sodium saccharinate.

When the composition is an emulsion, the proportion of the fatty phase can range from 5% to 80% by weight and preferably from 5% to 50% by weight, with respect to the total weight of the composition. The oils, waxes, emulsifiers and coemulsifiers used in the composition in the emulsion form are chosen from those conventionally used in the cosmetics field. The emulsifier and coemulsifier are present in the composition in a proportion ranging from 0.3% to 30% by weight and preferably from 0.5% to 20% by weight, with respect to the total weight of the composition. In addition, the emulsion can comprise lipid vesicles.

When the composition is an oily solution or gel, the fatty phase can represent more than 90% of the total weight of the composition.

In a known way, the cosmetic composition can also comprise adjuvants conventional in the cosmetics field, such as hydrophilic or lipophilic gelling agents, hydrophilic or lipophilic additives, preservatives, antioxidants, solvents, fragrances, fillers, screening agents, odour absorbers and colouring materials. The amounts of these various adjuvants are those conventionally used in the cosmetics field and, for example, from 0.01% to 10% of the total weight of the composition. These adjuvants, depending on their nature, can be introduced into the fatty phase, into the aqueous phase and/or into the lipid spherules.

Mention may be made, as oils or waxes which can be used in the invention, of mineral oils (liquid petrolatum), vegetable oils (liquid fraction of shea butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin wax. Fatty alcohols and fatty acids (stearic acid) can be added to these oils.

Mention may be made, as emulsifiers which can be used in the invention, for example, of glyceryl stearate, polysorbate 60 and the PEG-6/PEG-32/glycol stearate mixture sold under the name Tefose® 63 by Gattefosse.

Mention may be made, as solvents which can be used in the invention, of lower alcohols, in particular ethanol and isopropanol, or propylene glycol.

Mention may be made, as hydrophilic gelling agents which can be used in the invention, of carboxyvinyl polymers (carbomer), acrylic copolymers, such as acrylate/alkylacrylate copolymers, polyacrylamides, polysaccharides, such as hydroxypropylcellulose, natural gums and clays, and mention may be made, as lipophilic gelling agents, of modified clays, such as Bentones®, metal salts of fatty acids, such as aluminium stearates, and hydrophobic silica, ethylcellulose or polyethylene.

In an advantageous embodiment, the compositions according to the invention are oil-in-water (O/W) compositions, in particular compositions comprising lipophilic active principles. Such compositions are in particular based on oily globules provided with a lamellar liquid crystal coating, as described in Application EP 641 557. The cosmetic or dermatological composition is composed of an emulsion of the oil-in-water type formed of oily globules provided with a lamellar liquid crystal coating dispersed in an aqueous phase; each oily globule comprising at least one lipophilic compound which is active cosmetically or dermatologically is individually coated with a monolamellar or oligolamellar layer obtained from at least one lipophilic surface-active agent, from at least one hydrophilic surface-active agent and from at least one fatty acid, the coated oily globules having a mean diameter of less than 500 nanometres, and the aqueous phase comprises a basic agent in the dissolved state. When the compositions according to the invention are used for the cosmetic treatment of the keratinous substance, the active principle present in the oily phase is, for example, chosen from melanin regulators, liporegulators, antiseborrhoeic agents, antiageing agents, agents for combating UV radiation, keratolytic agents, antibacterial agents, antifungal agents, antidandruff agents, agents for combating hair loss, hair dyes, hair bleaches or conditioners.

Mention may be made, as examples of active principles for the treatment of the skin and/or hair which can be used in the context of the present invention, of the following compounds:

D-α-tocopherol, DL-α-tocopherol, D-α-tocopheryl acetate, DL-α-tocopheryl acetate, ascorbyl palmitate, vitamin F glycerides, vitamins D, vitamin $D_2$, vitamin $D_3$, retinol, retinyl esters, retinyl palmitate, retinyl propionate, β-carotene, D-panthenol, farnesol, farnesyl acetate, jojoba and blackcurrant oils which are rich in essential fatty acids, 5-(n-octanoyl)salicylic acid, salicylic acid, alkyl esters of α-hydroxy acids, such as citric acid, lactic acid or glycolic acid, asiatic acid, madecassic acid, asiaticoside, total extract of *Centella asiatica*, β-glycyrrhetinic acid, α-bisabolol, ceramides, such as 2-oleoylamino-1,3-octadecane, phytanetriol, milk sphingomyelin, phospholipids of marine origin rich in polyunsaturated essential fatty acids, ethoxyquin, rosemary extract, balm extract, quercetin, extract of dried microalgae (Algoxan Red from Algatec), octyl methoxycinnamate (Parsol MCX, Givaudan-Roure), butylmethoxydibenzoylmethane (Parsol 1789, Givaudan-Roure), octyl triazone (Uvinul T150, BASF), yellow, brown, black or red iron oxides, or titanium oxides, which can be provided in the micrometric or nanometric form or in the coated form.

The amount of biomass cultured on thermal water or of its extracts present in the compositions according to the invention will be adjusted by a person skilled in the art in order to obtain the desired activity, according to the type of extract used. By way of indication, the amount in the compositions will be between 0.001% and 10% by weight, with respect to the total weight of the composition, preferably from 0.01% to 5% by weight; in particular, it will be at least 0.1% by weight.

The invention also comprises a method for improving the condition of the skin and/or superficial body growths, in which at least one bacterium, capable of being obtained by culturing on a medium comprising a thermal or mineral water as are defined above, one of its extracts or a composition comprising them is applied to the skin and/or superficial body growths.

According to one of the aspects of the invention, it relates to a process for the preparation of a composition, in particular a cosmetic or dermatological composition, in which at least one bacterium, capable of being obtained by culturing on a medium comprising a thermal or mineral water as are defined above, or one of its extracts is mixed with at least one physiologically acceptable medium and adjuvants appropriate for the method of administration.

The invention will be illustrated in more detail in the following examples.

EXAMPLE 1

Preparation of the Biomass

Preparation of the Culture Medium

Composition:

| *Yeast extract | 2 g |
|---|---|
| *Soybean papain peptone | 2 g |
| *Glucose | 2 g |
| *Heller microelements | 2 ml |
| *$CaCl_2 \cdot 2H_2O$ | 66.21 mg |
| *Thermal water from La Roche-Posay | q.s. for 1 litre |

The pH of the medium is adjusted to 5.00 with a molar $H_3PO_4$ solution. The medium is sterilized by autoclaving at 121° C. for 30 minutes. After cooling to ambient temperature, the pH is readjusted to 7.20 by addition of a molar KOH solution.

Culturing:

After inoculating the medium at 1%, the culture is placed under orbital shaking at 100 revolutions/min and at 26° C. After growing for 48 hours, the culture is centrifuged at 8000 g for 15 minutes. The pellets are recovered and then autoclaved at 121° C. for 30 minutes. This biomass can be used for evaluation tests.

EXAMPLE 2

Comparison of the Effect of a Biomass Obtained with or without Thermal Water The aim of this study is to try to determine the effects on differential gene expression in human keratinocyte cultures of the biomass obtained by culturing on a culture medium reconstituted with osmotically treated water, of the biomass obtained by culturing on a medium reconstituted with thermal water from La Roche-Posay and of thermal water from La Roche-Posay.

Keratinocyte

| Product tested | Corneodesmosin | LEP16 |
|---|---|---|
| Biomass | — | — |
| Biomass LRP | +130% | +128% |
| Thermal water LRP | — | — |

In a keratinocyte culture, only the biomass cultured on thermal water from La Roche-Posay stimulates the expressions of the corneodesmosin and LEP16. The biomass cultured on osmotically treated water or the thermal water from La Roche-Posay do not have an effect on the expression of these marker genes for keratinocytes. In parallel, the ultrapure water from Merck used as control has no effect on the expression of the genes under consideration.

EXAMPLE 3

Differences in Expression Between the culturing of Vitreoscilla filiformis on Water from La Roche-Posay Versus the Culturing of Vitreoscilla filiformis on Osmotically Treated Water Two-dimensional electrophoresis was used as means for separating and visualizing the proteins expressed in the Vitreoscilla filiformis biomass, in one case cultured on water from La Roche-Posay and in the other case cultured on osmotically treated water.

This method of analysis consists in separating the proteins as a function of their pHi in a first "horizontal" dimension (this is isoelectric focusing or IEF). This separation takes place via a gel comprising an immobilized pH gradient, also known as IPG strips.

The proteins are subsequently separated as a function of their molecular weights in a second "vertical" migration dimension. The results show that the 2D gels are very rich in proteins; the latter are distributed in a molecular weight range between 6 kDa and 100 kDa, with an abundance of proteins in the region of acidic pH values. The rapid analysis of the image shows 6 different spots, on the one hand, the overexpression of two proteins in the biomass cultured on water from La Roche-Posay and, on the other hand, 4 proteins which appear to be more expressed in the biomass cultured on osmotically treated water.

These results show that there exists a difference in level of expression of the proteins in the biomasses cultured on osmotically treated water in comparison with that cultured on water from La Roche-Posay.

EXAMPLE 4

Increase in the Growth with Water from Vittel

Tests on culturing Vitreoscilla filiformis in a 10-litre fermenter in continuous mode were carried out starting from media partially reconstituted with osmotically treated water (control test) and with mineral water from Vittel (at 2%). The degree of growth set by the continuous culturing method was fixed at 0.12 $h^{-1}$ and the culturing conditions were identical in the 2 tests. The biomass was concentrated by centrifuging a continuously harvested culture volume. The measurement of the absorbance at 600 nm makes it possible to monitor the growth of the culture. The sludges obtained were stabilized by autoclaving at 121° C. for 30 minutes. The solids content and the amount of sludges harvested make it possible, from the culture volume centrifuged, to determine the cell concentration (in g/l) of the corresponding culture.

Summarizing table for the tests:

| Solvent for reconstituting the concentrated culture medium | Culture volume (l) | Amount of sludges (g) | Solids content (%) | [cell] (g/l) | Absorbance (600 nm) |
|---|---|---|---|---|---|
| Osmotically treated water | 10.98 | 220 | 5.41 | 1.08 | 3.17 |
| Mineral water Vittel | 7.938 | 415 | 2.37 | 1.24 | 4.39 |

Conclusion:

In comparison with the control culture on a medium reconstituted with osmotically treated water, the use of water from Vittel improves the growth of the bacterium; the cell yield is increased by 13%.

EXAMPLE 5

Composition Comprising a *Vitreoscilla filiformis* Extract

Phases A, B, C and D are prepared and successively mixed:

| Phase | | Amount (g) |
|---|---|---|
| A | PEG/PPG-18/18 dimethicone | 10 |
| A | Polysorbate 20 | 0.5 |
| A | Cyclopentasiloxane | 17 |
| A | Cetyl dimethicone | 6 |
| A | Tocopherol | 0.1 |
| A | Preservatives | 0.7 |
| B | Water | 25 |
| B | Magnesium sulphate | 1 |
| B | Glycerol | 7 |
| B | Propylene glycol | 3 |
| C | Water | 18.4 |
| D | Water | 10 |
| D | *Vitreoscilla filiformis* extract* | 1 |

*cultured according to Example 1 but on a medium comprising 1% of water from La Roche-Posay, the remainder being osmotically treated water.

The composition thus obtained can be applied morning and/or evening to the face, neck, hands and/or the whole of the body.

The invention claimed is:

1. A process for preparing a cosmetic or dermatological active principle, comprising:
    culturing at least one nonphotosynthetic and nonfruiting filamentous bacterium comprising an envelope on a medium comprising at least one first water which is thermal water from La Roche-Posay, the first water being mixed with at least one second water which is an osmotically treated and/or distilled water and the concentration of the first water is from 0.5% to 50% with respect to the second water to produce a cultured bacterium comprising an envelope, wherein the at least one first water exhibits a total mineral content of greater than or equal to 400 mg/l;
    separating the cultured bacterium from the medium, and rupturing the envelope of the cultured bacterium to produce the active principle.

2. The process according to claim 1, wherein a genus of the bacterium is the genus *Vitreoscilla*.

3. The process according to claim 2, wherein a specie of the bacterium is the specie, *Vitreoscilla filiformis*.

4. The process according to claim 3, wherein the bacterium is the strain deposited at the ATCC under the reference ATCC15551.

5. The process according to claim 1, wherein a concentration of calcium ions in the first water is greater than or equal to 100 mg/l.

6. The process according to claim 1, wherein a concentration of hydrogen-carbonates in the first water is greater than or equal to 300 mg/l.

7. The process according to claim 1, comprising:
    fermenting the cultured bacterium in the medium prior to separating the cultured bacterium from the medium to produce a fermented cultured bacterium; and
    separating the fermented cultured bacterium from the medium to recover a mass of the bacteria;
    wherein
    the medium further comprises a monosaccharide, and
    the bacterium is of the order *Beggiatoales*.

8. The process according to claim 7, further comprising: stabilizing the mass of the bacteria which is recovered after fermentation.

9. The process according to claim 1,
    wherein
    the medium comprises a mixture of (i) osmotically treated or distilled water and of (ii) thermal water, and
    a ratio (i)/(ii) is between 1 and 100.

10. The process according to claim 1, wherein the at least one first water exhibits a total mineral content of 400 mg/1 to 900 mg/l.

11. The process according to claim 1,
    wherein
    the medium comprises a mixture of (i) osmotically treated or distilled water and of (ii) thermal water, and
    a ratio (i)/(ii) is between 1 and 25.

12. A process for preparing a cosmetic or dermatological active principle, comprising:
    culturing at least one nonphotosynthetic and nonfruiting filamentous bacterium on a medium comprising at least one first water which is thermal water from La Roche-Posay, the first water being mixed with at least one second water which is an osmotically treated and/or distilled water and the concentration of the first water is from 0.5% to 50% with respect to the second water to produce a cultured bacterium, wherein the at least one first water exhibits a total mineral content of greater than or equal to 400 mg/l; and
    separating the cultured bacterium from the medium to prepare an extract of the medium, wherein the extract is the active principle.

13. The process according to claim 12, wherein the extract is supernatant from the medium.

14. The process according to claim 1, wherein the concentration of the first water is from 0.5% to 20% with respect to the second water.

15. The process according to claim 1, wherein the concentration of the first water is from 0.5% to 2% with respect to the second water.

16. The process according to claim 12, wherein the concentration of the first water is from 0.5% to 20% with respect to the second water.

17. The process according to claim 12, wherein the concentration of the first water is from 0.5% to 2% with respect to the second water.

* * * * *